United States Patent

Cognacq et al.

[11] 4,234,742
[45] Nov. 18, 1980

[54] BIS-(ARYLOXYCARBOXYLIC ACID) COMPOUNDS

[75] Inventors: Jean C. Cognacq, Maule; Jean Lacrampe, Courbevoie, both of France

[73] Assignee: Hexachimie, France

[21] Appl. No.: 45,665

[22] Filed: Jun. 5, 1979

[30] Foreign Application Priority Data

Jun. 14, 1978 [FR] France .................... 78 17814

[51] Int. Cl.³ .................. C07C 149/40; A61K 31/185
[52] U.S. Cl. ...................... 562/426; 424/317; 560/9; 560/57; 562/468
[58] Field of Search ............... 562/468, 471, 466, 452, 562/426; 424/308

[56] References Cited

U.S. PATENT DOCUMENTS

| | | | |
|---|---|---|---|
| 2,444,594 | 7/1948 | Day | 562/468 |
| 2,541,003 | 2/1951 | Day | 562/468 |
| 2,565,171 | 8/1951 | Faith | 562/468 |
| 3,169,144 | 2/1965 | Cavallini | 562/471 |
| 3,470,235 | 9/1969 | Jackson | 562/466 |
| 3,630,715 | 12/1971 | Gultag | 562/468 |
| 3,686,271 | 8/1972 | Lefon | 562/452 |
| 3,716,583 | 2/1973 | Nakamura | 562/468 |
| 4,088,474 | 5/1978 | Matterstock | 562/468 |
| 4,148,915 | 4/1979 | Thuillier | 562/426 |

*Primary Examiner*—Natalie Trousof
*Assistant Examiner*—Michael Shippon
*Attorney, Agent, or Firm*—Bacon & Thomas

[57] ABSTRACT

Compounds of the formula:

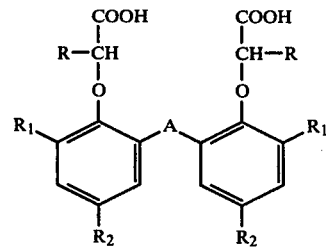

in which A is a methylene group, sulphur or a disulphide bridge, R is a hydrogen atom or a methyl group, $R_1$ is a linear or branched alkyl group having 1 to 4 carbon atoms, and $R_2$ is an alkyl group having 1 to 4 carbon atoms, or a halogen atom, or an alkoxy group, and their pharmaceutically acceptable salts have a valuable hypocholesterolemia-inducing activity.

2 Claims, No Drawings

BIS-(ARYLOXYCARBOXYLIC ACID) COMPOUNDS

DESCRIPTION

The present invention relates to new bis-(aryloxycarboxylic acid) compounds, to their preparation and to their use, in particular in therapy.

These new compounds are of the general formula (I):

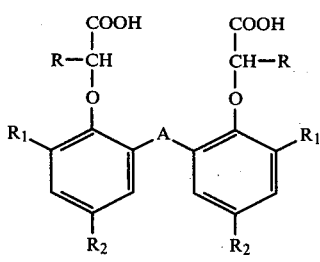

in which A is a methylene group, sulphur or a disulphide bridge, R is hydrogen or a methyl group, $R_1$ is a linear or branched alkyl group having 1 to 4 carbon atoms, and $R_2$ is an alkyl group having 1 to 4 carbon atoms, advantageously a methyl group, or a halogen atom, preferably chlorine, or an alkoxy group, advantageously a methoxy group, and pharmaceutically acceptable salts thereof.

The above-defined compounds possess pharmacological properties which render them valuable in therapy. They are especially active in the treatment of atherogenic hyperlipidemia. The invention therefore includes pharmaceutical compositions containing a compound of formula (I) or pharmaceutically acceptable salts thereof in association with a pharmaceutically acceptable excipient.

The present invention also includes a process for the preparation of the above-defined compounds, which process comprises forming an alkali metal, especially sodium, di-salt of a phenol of general formula (II):

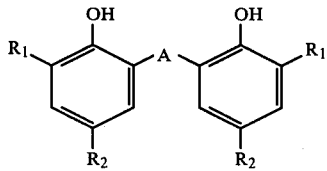

in which A, $R_1$ and $R_2$ are as defined above, reacting the di-salt with about two equivalents of a halocarboxylic acid ester of general formula (III)

in which X is a halogen atom, R is as defined above and $R_3$ is a lower alkyl group, hydrolysing the resulting ester to produce the acid and if desired converting the acid into a pharmaceutically acceptable salt. The di-salt of the phenol (II) can be formed by reacting the phenol with about 2 equivalents of an agent for introducing sodium, for example sodium hydride, sodium methoxide, sodium ethoxide or the like, in an electron-donating solvent, preferably N,N-dimethylformamide or dimethylsulphoxide. The reaction temperature is preferably about 20° C. to about 40° C. The halocarboxylic acid ester (III) is preferably a bromocarboxylic acid ester (X=Br). A methyl or ethyl ester ($R_3$=methyl or ethyl) is preferred. The ester is preferably heated in order to react it with the di-salt, desirably at a temperature of about 50 to about 90° C., most preferably about 70° C. The resulting ester is then hydrolysed, preferably by heating with sodium hydroxide or potassium hydroxide in an organic solvent, e.g. under reflux in methanol or ethanol.

Pharmaceutically acceptable salts of the free acid compounds (I) can be obtained in the conventional manner from the free acids.

The following non-limiting Examples are given in order to illustrate the invention.

EXAMPLE 1

Bis-(2-carboxymethoxy-3-t-butyl-5-methylphenyl) sulphide formula (I) with: R=H; $R_1$=t-butyl; $R_2$=$CH_3$; and A=S 4.5 g of a 50% strength suspension of sodium hydride in vegetable oil are added, in several portions, to a solution of 14.3 g (0.04 mol) of 2,2'-thio-bis-(4-methyl-6-tert.-butyl-phenol) in 100 ml of anhydrous dimethylformamide and the mixture is stirred thoroughly for 1 hour at 40° C.

9.8 g (0.08 mol) of ethyl chloroacetate are then added slowly; the reaction is exothermic. The solution is stirred for 1 hour at ambient temperature and then for 5 hours at 50° C., after which it is poured into 250 ml of water.

The mixture is extracted with ether, the ether extract is dried over magnesium sulphate and the solvent is evaporated off in vacuo.

The resulting residue (18.4 g) is treated under reflux for 7 hours with 3 g (0.075 mol) of sodium hydroxide pellets in 150 ml of ethanol.

The ethanol is then evaporated off. The residue is taken up in water and the resulting solution is extracted with ether.

The aqueous phase is then acidified to pH 1 and extracted with ether. The ether phase is dried over magnesium sulphate and evaporated; this yields 7.2 g of a residue which is recrystallised from cyclohexane to give 5.1 g of the expected product which melts at 207° C.

EXAMPLE 2

Bis-(2-α-carboxyethoxy-3-t-butyl-5-methylphenyl) sulphide formula (I) with: R=$CH_3$; $R_1$=t-butyl; $R_2$=$CH_3$; and A=S The method of operation is identical to that of the preceding example, except that 21.5 g (0.06 mol) of 2,2'-thio-bis-(4-methyl-6-tert.-butyl-phenol), 6.8 g of a 50% strength suspension of sodium hydride, in 150 ml of anhydrous dimethylformamide, and 15.7 ml of ethyl 2-bromopropionate are used as the starting materials.

The resulting evaporation residue (29.2 g) is treated with 5 g of sodium hydroxide pellets in 150 ml of ethanol.

23.9 g of a crude product are isolated and this product is recrystallised from pentane. This gives 12.2 g of the expected product which melts at 149° C.

EXAMPLE 3

Bis-(2-α-carboxyethoxy-3-methyl-5-chlorophenyl) sulphide formula (I) with: R=$CH_3$; $R_1$=$CH_3$; $R_2$=Cl; and A=S The method of operation is identical to that of Example 1, except that 20.4 g (0.065 mol) of 2,2'-thio-bis-(4-chloro-6-methylphenol), 7.4 g of a 50% strength suspension of sodium hydride, in 150 ml of anhydrous dimethylformamide, and 17 ml of ethyl 2-bromopropionate are used as the starting materials.

The resulting evaporation residue (21.6 g) is treated with 5 g of sodium hydroxide pellets in 250 ml of ethanol.

16.1 g of crude product are isolated and this product is recrystallised from cyclohexane. This gives 11.6 g of the expected compound which melts at 135° C.

EXAMPLE 4

(2,2'-Di-[α-carboxyethoxy]-3,3'-dimethyl-5,5'-dichloro)-diphenylmethane formula (I) with: R═CH₃; R₁═CH₃; R₂═Cl and A═CH₂

The method of operation is identical to that of Example 1, except that 11.8 g (0.04 mol) of 2,2'-methylene-bis-(4-chloro-6-methylphenol), 4.2 g of a 50% strength suspension of sodium hydride, in 100 ml of anhydrous dimethylformamide, and 12.6 ml of ethyl 2-bromopropionate are used as the starting materials.

The resulting evaporation residue (18 g) is treated with 5 g of sodium hydroxide pellets in 50 ml of ethanol.

8.3 g of the expected resulting product are isolated, after recrystallisation from a mixture of cyclohexane and isopropyl ether (90/10), and this product melts at 178° C.

The hypocholesterolemia-inducing activity is investigated on male Sprague Dawley rats weighing 130 g. The products studied are administered orally for four days at a daily dose of 250 mg/kg.

On the fifth day, the animals are sacrificed and the degree of cholesterolemia is determined in accordance with the method of Watson.

The activity of the known product referred to as "clofibrate" was studied in this test under the same conditions.

The table below gives the mean and the standard deviation from the mean of the degrees of cholesterolemia obtained after treatment.

| Batch | Number of animals | Degree of cholesterolemia g.liter⁻¹ - mean - standard deviation from the mean |
| --- | --- | --- |
| Control | 10 | 1.113 |
|  |  | 0.037 |
| Compound of Example 1 | 10 | 0.847 |
|  |  | 0.053 |
| Compound of Example 2 | 10 | 0.693 |
|  |  | 0.027 |
| Clofibrate | 10 | 0.854 |
|  |  | 0.053 |

The toxicity studies carried out on Sprague Dawley rats after oral administration made it possible to determine a zero lethal dose of more than 1,600 mg/kg for the two products studied above.

In conclusion, the compounds defined above possess a valuable hypocholesterolemia-inducing activity, the activity/toxicity ratio permitting their therapeutic use, as sugar-coated pills, in the treatment of atherogenic hyperlipidemia at unit doses of 150 to 250 mg per administration, at the rate of 4 administrations per day for an adult human being weighing about 70 kg.

We claim:

1. A compound of the formula

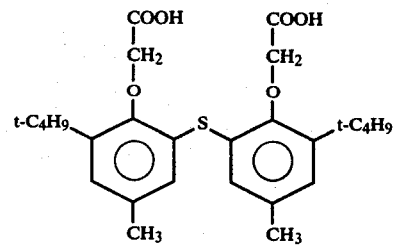

or a pharmaceutically acceptable salt thereof.

2. A compound of the formula

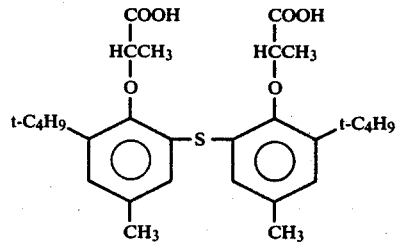

or a pharmaceutically acceptable salt thereof.

* * * * *